(12) United States Patent
Marshall et al.

(10) Patent No.: US 8,084,264 B2
(45) Date of Patent: Dec. 27, 2011

(54) METHOD FOR IDENTIFYING NAPHTHENATES IN A HYDROCARBON CONTAINING LIQUID

(75) Inventors: Alan G. Marshall, Tallahassee, FL (US); Priyanka Juyal, Tallahassee, FL (US); Mmilili M. Mapolelo, Tallahassee, FL (US); Ryan P. Rodgers, Tallahassee, FL (US)

(73) Assignee: Florida State University Research Foundation, Inc., Tallahassee, FL (US), ( * ) Notice: Subject to any disclaimer, the term of this patent is extended or adjusted under 35 U.S.C. 154(b) by 8 days.

(21) Appl. No.: 12/694,606

(22) Filed: Jan. 27, 2010

(65) Prior Publication Data

US 2010/0190260 A1 Jul. 29, 2010

Related U.S. Application Data

(60) Provisional application No. 61/147,659, filed on Jan. 27, 2009.

(51) Int. Cl.
*G01N 33/26* (2006.01)
*G01N 31/02* (2006.01)
*G01N 30/72* (2006.01)

(52) U.S. Cl. .......... 436/129; 436/60; 436/127; 436/139; 436/173; 436/174

(58) Field of Classification Search .............. 436/60–61, 436/127–129, 139–142, 173–174, 181
See application file for complete search history.

(56) References Cited

U.S. PATENT DOCUMENTS

| 6,531,055 | B1* | 3/2003 | Greaney | 208/263 |
| 6,627,069 | B2* | 9/2003 | Greaney | 208/263 |
| 7,507,329 | B2* | 3/2009 | Pinho et al. | 208/263 |
| 2002/0011430 | A1* | 1/2002 | Greaney | 208/226 |
| 2006/0201855 | A1* | 9/2006 | Pinho et al. | 208/263 |
| 2007/0298505 | A1* | 12/2007 | Smith et al. | 436/61 |
| 2010/0230587 | A1* | 9/2010 | Marshall et al. | 250/282 |

FOREIGN PATENT DOCUMENTS

GB 2436679 * 10/2007

OTHER PUBLICATIONS

Hsu, C. S. et al, Energy & Fuels 2000, 14, 217-223.*
Jones, D. M. et al, Analytical Chemisrty 2001, 73, 703-707.*
Hughley, C. A. et al, Organic Geochemistry 2002, 33, 743-759.*
Rudzinski, W. E. et al, Energy & Fuels 2002, 16, 1178-1185.*
Barrow, M. P. et al, Analytical Chemistry 2003, 75, 860-866.*
Gragryelski, W. et al, Analytical Chemistry 2003, 75, 4612-4623.*
Wu, Z. et al, Energy & Fuels 2005, 19, 1072-1077.*
Wang, Y. et al, Fuel 2006, 85, 2489-2493.*
Headley, J. V. et al, Analytical Chemistry 2007, 79, 6222-6229.*
Smith, B. E. Rapid Communications in Mass Spectrometry 2008, 22, 3909-3927.*
Mapolelo, M. M. et al, Energy & Fuels 2009, 23, 349-355 (Dec. 11, 2008 Web Publication).*
Mohammed, M. A. et al. Colloids and Surfaces A: Physicochemical and Engineering aspects 2009, 349, 1-18.*

* cited by examiner

*Primary Examiner* — Arlen Soderquist
(74) *Attorney, Agent, or Firm* — Novak Druce + Quigg LLP

(57) ABSTRACT

A method for quantifying the presence of naphthenic acids in a hydrocarbon-comprising liquid that includes: contacting a hydrocarbon-comprising liquid with gaseous ammonia; isolating a reaction product produced by the contacting step; and analyzing the reaction product for the presence of naphthenates using a mass spectrometry technique. The naphthenic acids known to form commercial naphthenate deposits can be (i) ions of tetraprotic carboxylic acids having molecular weights ranging from 1225 to 1270 Daltons, (ii) n-alkyl or branched carboxylic acids having molecular weights ranging from 250 to 650 Daltons, or (iii) both.

18 Claims, 15 Drawing Sheets

METHOD FOR IDENTIFYING NAPHTHENATES IN A HYDROCARBON CONTAINING LIQUID

CROSS-REFERENCE TO RELATED APPLICATIONS

This application claims priority to U.S. Provisional Application No. 61/147,659 filed Jan. 27, 2010, entitled "Method for Identifying Naphthenates in a Hydrocarbon Containing Liquid," the entirety of which is incorporated by reference herein.

STATEMENT REGARDING FEDERALLY SPONSORED RESEARCH OR DEVELOPMENT

The United States Government has rights in this invention pursuant to contract no. DMR 06-54118 between the National Science Foundation and Florida State University.

FIELD OF THE INVENTION

The invention relates to a method for detecting, identifying and quantifying the presence of residue forming naphthenic acids in a hydrocarbon comprising liquid.

BACKGROUND

Many oilfield operators are faced with challenges in flow assurance due to formation of deposits and soaps in the oilfield, generally termed naphthenates. Naphthenate deposits in crude oil production cause major problems for petroleum producers by obstructing pipelines and screens and causing production irregularities that result in unplanned and expensive production shutdowns. The problem of naphthenate deposits has recently become more pronounced as more oilfields that contain immature, heavy oils with higher naphthenic acid content begin production. Examples of oilfields associated with the formation of naphthenate deposits include those found offshore in Great Britain, West Africa, the North West Shelf in Australia, Bohai Bay in China, Kutei Basin in Indonesia and the Gulf of Mexico.

Naphthenate deposits form mainly during upstream operations, commonly at the oil/water cutoff point. Calcium and sodium naphthenate deposits are solid and emulsion-like deposits formed by the interaction of naphthenic acids and divalent ($Ca^{2+}$, $Fe^{2+}$ and $Mg^{2+}$) or monovalent ($Na^+$, $K^+$) ions present in produced waters. Calcium naphthenates occur as a viscous, sticky solid or sludge commonly found in oil-water separators and electrostatic treaters. Interestingly, calcium naphthenates harden when they are exposed to air and cooling. Crude oils with medium to heavy American Petroleum Institute (API) gravities (API values of 18-27° API) rich in naphthenic acids, with a high total acid number (TAN=0.80-8.0 mg KOH/(g oil)) are at risk to react with divalent cations to form calcium naphthenates, such as calcium naphthenate. In contrast to calcium naphthenates, naphthenates formed with monovalent cations occur as a very stable emulsion, soap, or sludge, and are associated with light API gravities (typically 32 to 41° API) crude oils with a low TAN (0.05-0.60) and high concentration of volatile fatty acids.

Naphthenic acids are saturated acyclic or cyclic carboxylic acids in which the carboxylic acid group is attached to the aliphatic side chain or a cycloaliphatic ring (single ring or multiple fused rings). The characterization of naphthenic acids has always been a challenge, especially for naphthenic acids associated with formation of naphthenate deposits. However, naphthenic acids found in Norwegian calcium naphthenate deposits are currently known by the generic name "ARN acids." ARN acids are tetraprotic naphthenic acids with molecular weights generally ranging from 1227 to 1235 Da. They are believed to include a head to head linked isoprenoid 20-bis-16, 16' biphytane carbon skeleton, with 4-6 cyclopentane rings. The homologous series of ARN acids corresponds to empirical formulas, $C_{80}H_{138}O_8$, $C_{80}H_{138}O_8$, $C_{80}H_{140}O_8$, $C_{80}H_{142}O_8$, $C_{80}H_{144}O_8$, and $C_{80}H_{146}O_8$ with double bound equivalent (DBE) values ranging from 8 to 12. As used herein, DBE refers to double bond equivalents and is equal to the number of rings plus the number of carbon double bonds, e.g., C═C, C═O, etc.

As ARN acids are tetraprotic carboxylic acids, a DBE range from 8 to 12 indicates 4 to 8 rings in the hydrocarbon structure. However, the presence of ARN acids does not guarantee the formation of naphthenate deposits. Currently, there is no means of predicting whether a crude oil composition will form naphthenate deposits until the naphthenate deposits are found in the crude oil operation. Once naphthenate deposits are discovered, shutdowns are required to remove the deposits and it would be expensive to retrofit the crude oil operation to reduce or eliminate the source of the deposits.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1A:
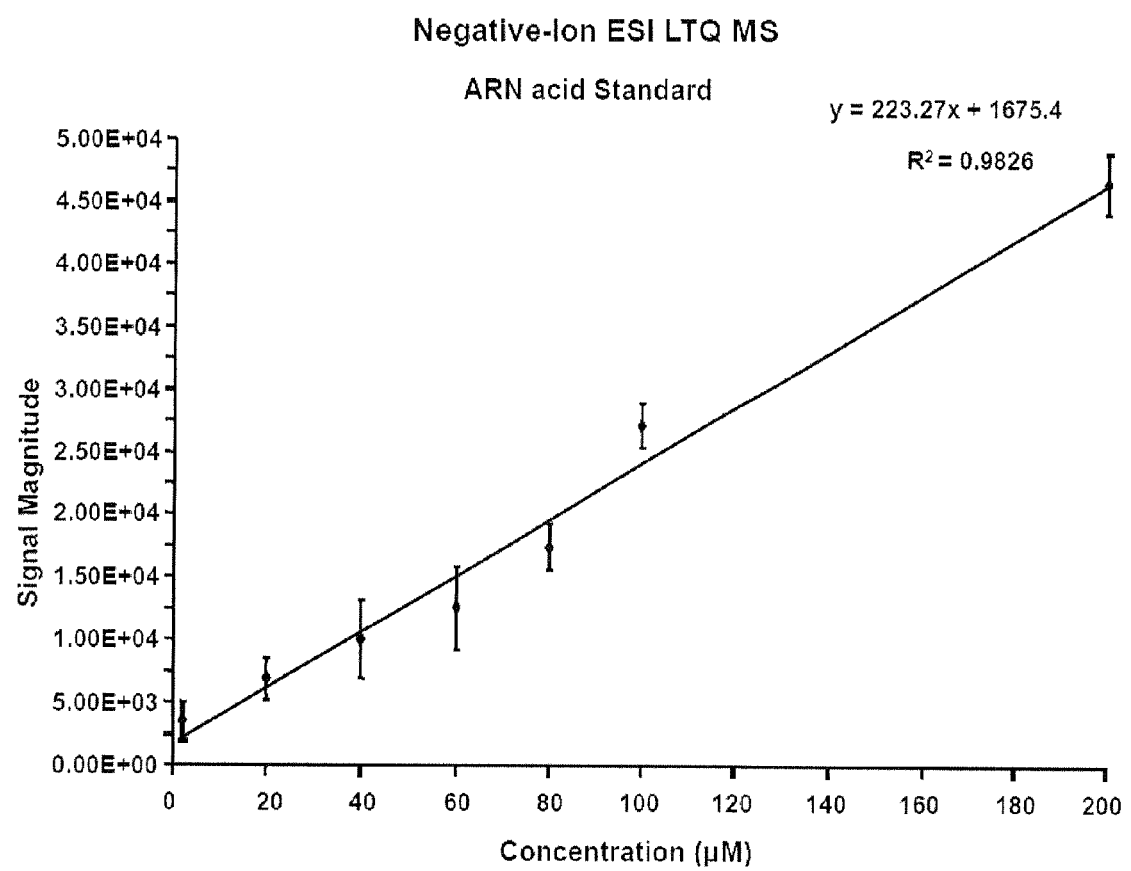
FIG. 1a is the quantitation of ARN species over the concentration range of 2-200 μM without a crude oil matrix (bitumen) and FIG. 1b is the quantitation of ARN species over the concentration range of 2-200 μM within a crude oil matrix (bitumen).

A method for quantifying the presence of naphthenic acids in a hydrocarbon comprising liquid. Because hydrocarbon comprising liquids, e.g., crude oil, include a variety of hydrocarbon and heteroatom containing hydrocarbon components, it is often difficult or impossible to identify specific compounds, such as naphthenic acids, present therein. The invention provides a method of accurately identifying naphthenic acid species, and relative amounts thereof, present in a hydrocarbon comprising liquid.

In one embodiment, the invention is drawn to a process for isolating and quantifying the presence of naphthenic acids in a hydrocarbon-comprising liquid. The method includes contacting a hydrocarbon-comprising liquid with gaseous ammonia in order to produce a reaction product, and then isolating the reaction product. The reaction product is then analyzed for the presence of naphthenates by use of an atmospheric pressure ionization mass spectrometry technique, including, but not limited to, electrospray ionization and photoionization techniques, e.g. atmospheric pressure photoionization and laser desorption ionization.

As used herein, the phrase "reaction product" refers to a product of the reaction between gaseous ammonia and a hydrocarbon-comprising liquid, e.g., crude oil or crude oil fraction. Reaction products can refer to commercial naphthenate deposits and other products produced when the hydrocarbon-comprising liquid is contacted with gaseous ammonia. Of particular interest are precipitates and emulsions that form as a result of contacting the hydrocarbon-comprising liquid with gaseous ammonia.

As used herein, "commercial naphthenate deposits" include deposits formed by the reaction of naphthenic acids, including ARN acids, with monovalent (e.g., $Na^+$, $K^+$) or divalent (e.g., $Ca^{2+}$, $Fe^{2+}$, $Mg^{2+}$) ions or with gaseous ammonia. Exemplary naphthenic acids known to form commercial naphthenate deposits include tetraprotic naphthenic carboxylic acids having molecular weights ranging from 1225 to 1270 Daltons, and n-alkyl or branched carboxylic acids having molecular weights ranging from 250 to 650 Daltons. In general, the high molecular weight, tetraprotic naphthenic carboxylic acids react with gaseous ammonia to form a solid precipitate, whereas the lower molecular weight n-alkyl or branched carboxylic acids form an emulsion, soap or sludge.

The n-alkyl or branched carboxylic acids having molecular weights ranging from 250 to 650 Daltons can be linear or branched carboxylic acids and can be monoprotic or diprotic. These lower molecular weight naphthenic acids are involved in the formation of sodium naphthenate deposits and are believed to include monoprotic naphthenic acids including 15-30 carbon atoms.

The hydrocarbon-comprising liquid can include crude oil. For example, the hydrocarbon-comprising liquid can be any liquid including hydrocarbons, such as crude oil, bitumen, a crude oil fraction, a crude oil concentrate, a crude oil extract, a diluted crude oil, or any other product of crude oil or other similar raw materials.

The duration of the contacting step can be sufficient to produce an ammonium naphthenate salt in the hydrocarbon-comprising liquid. The duration of the contacting step can be any appropriate duration sufficient to produce an ammonia naphthenate salt in the hydrocarbon-comprising liquid containing one or more naphthenic acids. For example, the duration can be at least 30 minutes, at least one hour, at least two hours, or at least three hours.

The process can also include an aging step between the contacting step and the isolating step. The aging step can include cooling the hydrocarbon-comprising liquid to a temperature of 10° C. or less for a period of at least 1 hour. The cooling temperature can by any temperature sufficient to facilitate formation or consolidation of reaction products, such as commercial naphthenate deposits. For example the cooling temperature can be 0° C. or less, −10° C. or less, −25° C. or less, or −50° C. or less. The minimum cooling temperature can be any temperature above the freezing point of the gaseous ammonia treated hydrocarbon-comprising liquid. For example, the minimum cooling temperature can be −200° C., −150° C., or −100° C. The duration of the cooling period can be at least 1 hour, at least 2 hours, or at least 4 hours.

By definition, the reaction products can take on a variety of forms, including a precipitate and an emulsion. For isolation of a precipitate reaction product, any number of techniques known in the art, for example filtering, decanting and sedimentation, can be useful. For isolation of an emulsion reaction product, any number of techniques known in the art, including liquid-liquid extraction, can be useful. The isolation step can include multiple sub-steps in order to process the reaction product in proper form for analysis. As an example, it may be necessary to separate the emulsion phases into a naphthenate-rich phase and a naphthenate-deficient phase so that the naphthenate-rich phase can be isolated and analyzed. Any number of additional isolating steps can also be used including, but not limited to, purifying, separating, and washing.

Even after isolation, the reaction product may require subsequent processing prior to the analyzing step. For example, the reaction product can be dissolved, digested, or both, in order to convert the reaction product to an appropriate form for any one of a number of ionization methods used with mass spectrometry.

The process can also include a drying step after the naphthenate containing reaction product is isolated and digested. For example, the reaction product may undergo acid digestion, followed by an organic extraction (e.g., using toluene) to extract the naphthenic acids from the naphthenates. The organic phase, which will include the naphthenic acids, can then be subjected to a drying step to remove trace water from the organic phase. For example, the hydrocarbon-comprising liquid can be dried in anhydrous magnesium sulfate ($MgSO_4$) or with a stream of nitrogen gas.

Exemplary ionization methods for use with mass spectrometry include, but are not limited to, ionization techniques selected from the group consisting of an electrospray ionization, a photoionization, chemical ionization, electron ionization, fast atom bombardment ionization, field ionization, field desorption/ionization, or a combination thereof.

The ionization technique can utilize any number of techniques, such as electrospray ionization and photoionization, useful in conjunction with mass spectrometers and mass analyzers. The evaluation step can include comparing mass spectrometry results of the reaction product to standards for naphthenic acids known to form commercial naphthenate deposits. Exemplary mass spectrometry techniques that can be useful in the methods disclosed herein include, but are not limited to, Fourier transform ion cyclotron resonance mass spectrometer, an ion trap mass spectrometer, a quadrupole mass spectrometer, an orbitrap mass spectrometer, a time-of-flight mass spectrometer or a magnetic sector mass spectrometer.

Based on investigations developed for this invention, it has been determined that naphthenic acids that form commercial naphthenate deposits include, but are not limited to, (i) ions of tetraprotic carboxylic acids having a molecular weight ranging from 1225 to 1270 Daltons, and (ii) n-alkyl or branched carboxylic acids having a molecular weight ranging from 250 to 650 Daltons. The n-alkyl or branched carboxylic acids forming commercial naphthenate deposits can be monoprotic or diprotic.

The tetraprotic naphthenic carboxylic acids known to form commercial naphthenate deposits can be tetraprotic carboxylic acids of Formula I:

$$C_nH_{2(n+1-DBE)}O_8 \quad (I)$$

In the above formula, n=77-85 and DBE=8-12. The number of rings in the tetraprotic carboxylic acids of Formula I can be between 4 and 8 with the remaining four DBE's being carbonyl groups (C=O) in each of the four carboxylic acid functionalities of the naphthenic acid.

In another embodiment, the invention is drawn to a method for determining whether a crude oil composition will produce commercial naphthenate deposits during crude oil processing. The method of determining whether commercial naphthenate deposits will form can include contacting the crude oil composition with gaseous ammonia and, if a reaction product forms, isolating a reaction product produced by said contacting step. The reaction product can be analyzed for the presence of naphthenic acid salts by use of a-mass spectrometry technique. The analysis step can include comparing mass spectrometry results of the reaction product to standards for naphthenic acids known to form commercial naphthenate deposits. If no reaction product is formed, it can be concluded that the crude oil composition is not likely to form commercial naphthenate deposits. The crude oil composition can form commercial naphthenate deposits during crude oil processing if the analysis indicates that the reaction product includes a naphthenic acid ion present in commercial naphthenate deposits.

In yet another embodiment, the invention is drawn to a method of operating a crude oil operation to avoid the formation of naphthenate deposits. The method of operating the crude oil operation can include contacting a crude oil mixture used in a crude oil operation with gaseous ammonia and isolating a reaction product produced by the contacting step. The reaction product can be analyzed for the presence of naphthenic acid ions present in commercial naphthenate deposits by mass spectrometry. The mass spectrometry results can be compared to mass spectrometry standards for naphthenic acid ions present in commercial naphthenate deposits. If the comparing step indicates that the reaction product comprises a naphthenic acid ion present in commercial naphthenate deposits, the composition of the crude oil mixture can be adjusted to reduce the formation of commercial naphthenate deposits.

As used herein, "crude oil operation" is used to describe any operation in which crude oil is processed or transported including, but not limited to, oil wells, oil pipelines, oil tankers, oil containers, and oil refineries. As used herein, "crude oil mixture" is used to describe the mixture of crude oil and other constituents found in the crude oil-containing composition flowing through a crude oil operation. Crude oil mixtures often contain additives and production water, which is often injected into the ground in order to extract crude oil from underground reserves. Additional components that can be found in crude oil mixtures include, but are not limited to, viscosity modifiers, surfactants, solvents, miscible gases and various contaminants and impurities.

The crude oil mixture can include production water and the treating step can include, (i) modifying a pH of the production water or the crude oil mixture, (ii) reducing in the production water or the crude oil mixture a concentration of one or more ions selected from the group consisting of $Ca^{2+}$, $Fe^{2+}$, $Mg^{2+}$, $Na^+$ and $K^+$, or (iii) both. The inventors have discovered that, if naphthenic acids are present in the crude oil being extracted, formation of commercial naphthenate deposits can be prevented by avoiding the introduction of monovalent and divalent cations to the crude oil mixture. In addition, cations that lead to the formation of commercial naphthenate deposits, such as $Ca^{2+}$, $Fe^{2+}$, $Mg^{2+}$, $Na^+$ and $K^+$, can be traced to production water pH and cations present in the production water.

In one exemplary treatment approach, the production water can be treated with an amount of acid sufficient to prevent the cations from forming commercial naphthenate deposits where the production water is subsequently injected into a hydrocarbon-comprising liquid, such as crude oil. Alternatively, the production water can undergo a pre-treatment to remove the cations involved in commercial naphthenate deposit formation. The cations can be removed by any technique having the desired effect including, but not limited to, water softening, desalination, adding a descaling agent, and other water purification techniques.

EXAMPLE 1

Precipitation of Naphthenic Acids

Preconcentration

A three-necked 250 ml round bottom flask was used to bubble ammonia to the crude oil solution. The round bottom flask was equipped with a tapered gas inlet-tube on one neck in such as way that the tip of the gas-inlet tube is immersed in the crude oil solution. A thermometer tube is fixed on the second side neck. In order to control the gas pressure inside the reaction flask, a thistle funnel was fixed to the central neck of the flask as a pressure vent. 2-4 g of crude oil was dissolved in 25 mL of toluene (in some instances a mixture of toluene and heptane 50:50 (vol:vol)) in a 3-necked round bottom flask. The reaction flask was placed in an ice-bath mounted on a magnetic stir plate. The sample solution was stirred with a magnetic stir bar and purged with dry nitrogen gas for 30 minutes. Anhydrous ammonia gas was introduced (purged) slowly and with continuous stirring for 2 hrs in an ice-bath. The temperature of the bath was subsequently raised to 50° C. and ammonia purging continued for additional 1 hr. The ammoniated crude oil was left to cool at room temperature and further cooled overnight at temperature below 0° C. Crystals or sludge were isolated from the crude oil and washed with cold toluene to remove traces of the crude oil. In some instances the sludge was isolated by first decanting the crude oil fraction. The crystals were then dissolved in methanol and analyzed by negative ion electrospray ionization (ESI) FT-ICR-MS.

EXAMPLE 2

Materials and Methods for Evaluation of Naphthenate Deposits

Two field calcium naphthenate deposits and one sodium naphthenate emulsion sample from a crude oil processing system were analyzed. The calcium naphthenate samples were collected from production separators in which naphthenate deposits were reported. A sodium naphthenate deposit generated in the laboratory was prepared as follows. A crude oil sample was received and used as received. To form an emulsion, 100 mL of crude oil was transferred into a 250 mL flask along with 50 mL of synthetic brine consisting of 2000 ppm (0.2 wt-%) $Na^+$ and 0.1 g of $NaHCO_3$. The mixture was agitated briefly by hand (~5-10 minutes) and allowed to settle for 2 days. Afterwards, a biphasic mixture of 50% oil and 50% emulsion was noted. The emulsion was sampled at the midpoint of the emulsion layer for subsequent analysis.

Extraction of Naphthenic Acids from Naphthenate Deposits

Calcium naphthenate samples were preweighed (~100 mg) and washed with toluene to remove entrapped crude oil. The samples were repeatedly washed until the color of the toluene phase was almost clear. After the toluene wash, half of the samples were subjected to another wash with methylene chloride.

The sodium naphthenate samples were not subjected to the wash procedure. After the associated deposits were isolated (sodium naphthenate) and cleaned (calcium naphthenate), they were digested with 1 M hydrochloric acid (HCl) or 5 M glacial acetic acid ($CH_3COOH$) followed by toluene extraction. The acidic digests were redissolved in 50:50 (vol:vol) toluene: methanol for negative-ion ESI FT-ICR MS analysis.

Quantitation

Figure 1B:
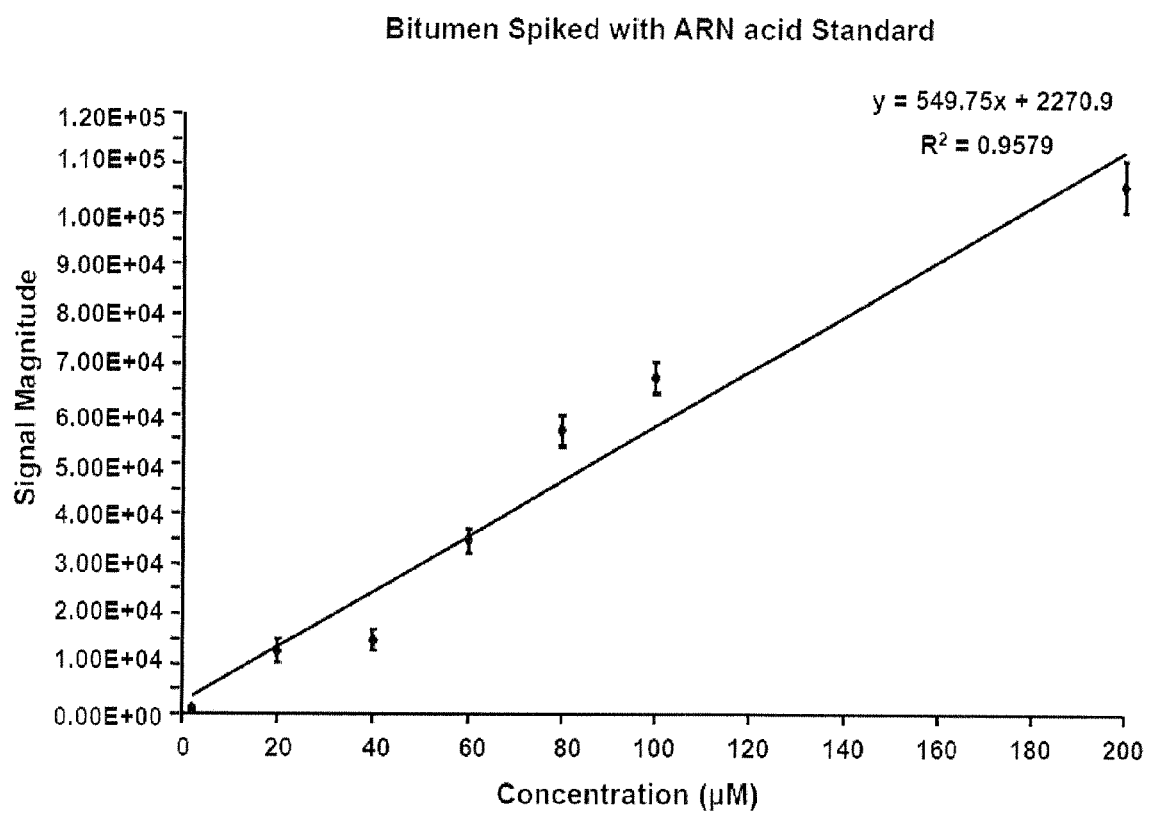

Three crude oils known to produce calcium naphthenate deposits were spiked with a pure ARN acid standard previously isolated from a solvent-cleaned naphthenate deposit followed by acid digestion. Bitumen exhibiting no deposits was used as a control and was also spiked with a pure ARN acid standard previously isolated from a solvent-cleaned naphthenate deposit followed by acid digestion. Analysis of the ARN acid standard by negative-ion ESI MS showed only ARN acid species. The ARN acid standard was spiked at concentrations ranging from ~2-200 micromolar into the whole crude oils to determine the broadband MS detection limit. For those concentrations at or just below the broadband detection limit, a modified extraction procedure was performed to preconcentrate the acidic species. Samples were analyzed by negative-ion electrospray ionization (ESI) with a LTQ (ThermoFisher) ion trap. FIGS. 1a and 1b show that the mass spectral response is linear (allows quantitation) for both the pure ARN standard (FIG. 1a) as well as ARN species in a crude oil matrix (bitumen) (FIG. 1b) over the concentration ranges tested. The results suggest that quantitation of ARN species is possible for both clean ARN deposits and those that contain entrained oil.

Results and Discussion

Figure 2A:
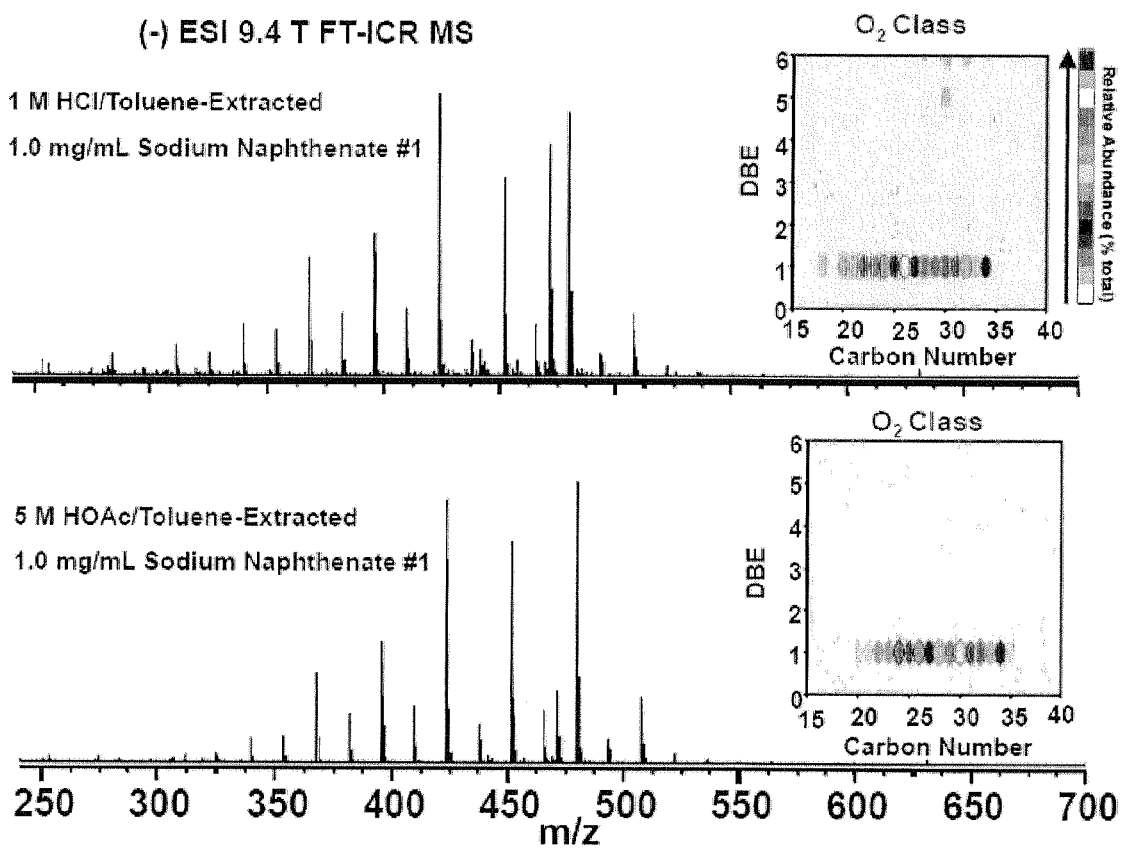
FIGS. 2a and 2b are broadband negative-ion ESI 9.4 T FT-ICR mass spectra for two different field sodium naphthenate deposit samples, extracted by toluene acidified with either acetic acid or hydrochloric acid.
Figure 2B:
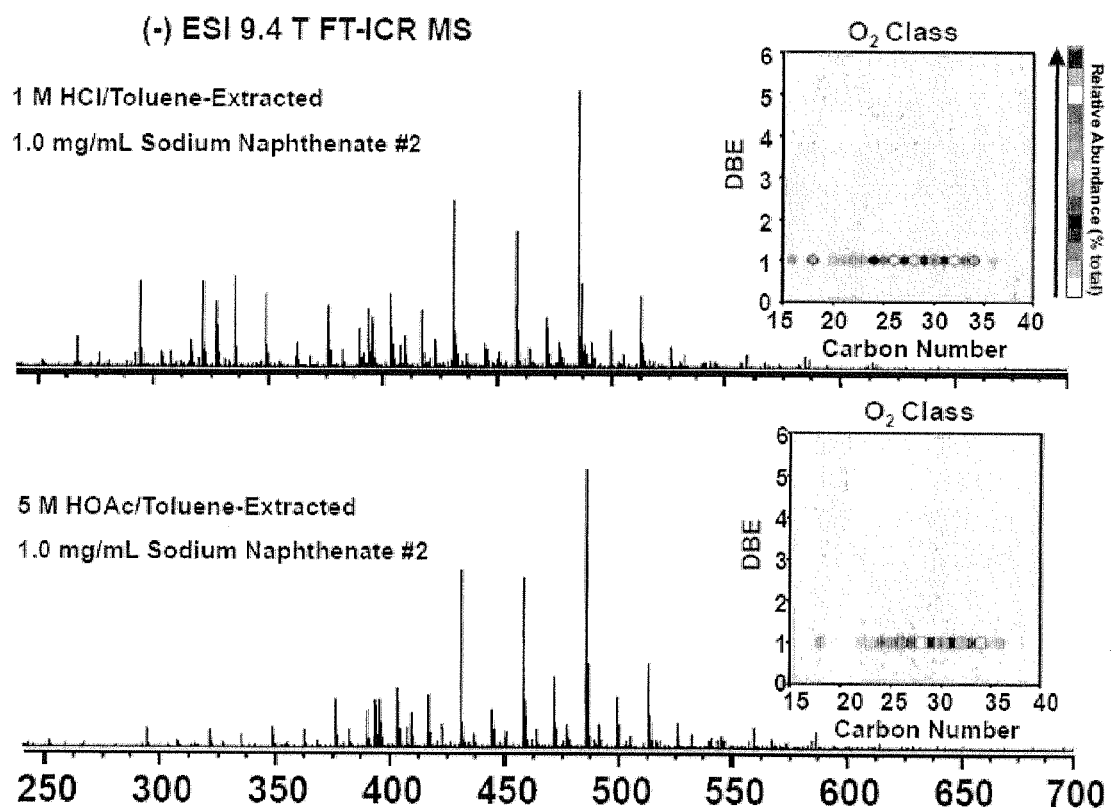

Analysis of the naphthenate deposits identified acidic species that selectively accumulate and thus are assumed to participate in naphthenate formation. Calcium naphthenate samples were largely composed of a family of tetraprotic acids (ARN acids) whereas the sodium naphthenate deposits contained mostly low DBE saturated naphthenic acids. FIGS. 2a and 2b show broadband negative-ion ESI 9.4 Tesla FT-ICR mass spectra of two sodium naphthenate samples. Although the mass spectra of the samples are quite similar, the mass spectra of sodium naphthenate sample #2 (NaN #2) (FIG. 2b) seem to be more complex and extend to higher m/z relative to sodium naphthenate sample #1 (NaN #1) (FIG. 2a.). In sodium naphthenate sample #1 (NaN #1), the molecular weight of the extracted naphthenic acids ranged from 250 to 550 Dalton (Da), whereas the molecular weight of extracted naphthenic acids in sodium naphthenate sample #2 (NaN #2) ranged from 250 to 650 Da. These results demonstrate that the sodium naphthenate deposit consisted mainly of low molecular weight naphthenic acids, primarily acyclic saturated fatty acids (displayed as color compositional images to the right of the mass spectra) with molecular weights in the range of 250 to 650 Da.

Sodium naphthenates have frequently been reported as emulsions and are sodium salts of n-alkyl or slightly branched carboxylic acids (fatty acids), e.g., RCOONa. It is believed that when crude oils contact $NaHCO_3$-laden production waters at high pH, saponification takes place producing the sodium salts of the fatty acids that cause commercial sodium naphthenate deposits.

Figure 3A:
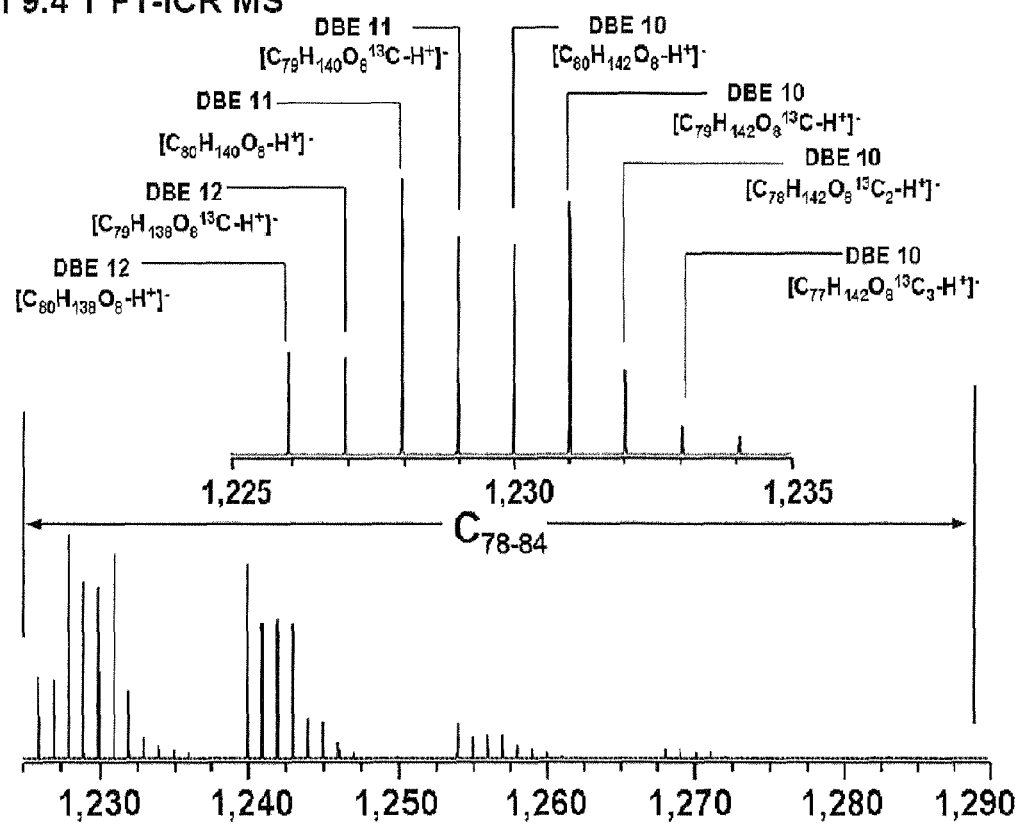
FIGS. 3a and 3b are negative-ion ESI FT-ICR mass spectra of a HCl acidified toluene extracted calcium naphthenate deposit, with FIG. 3a being a zoom mass inset of FIG. 3b.
Figure 3B:
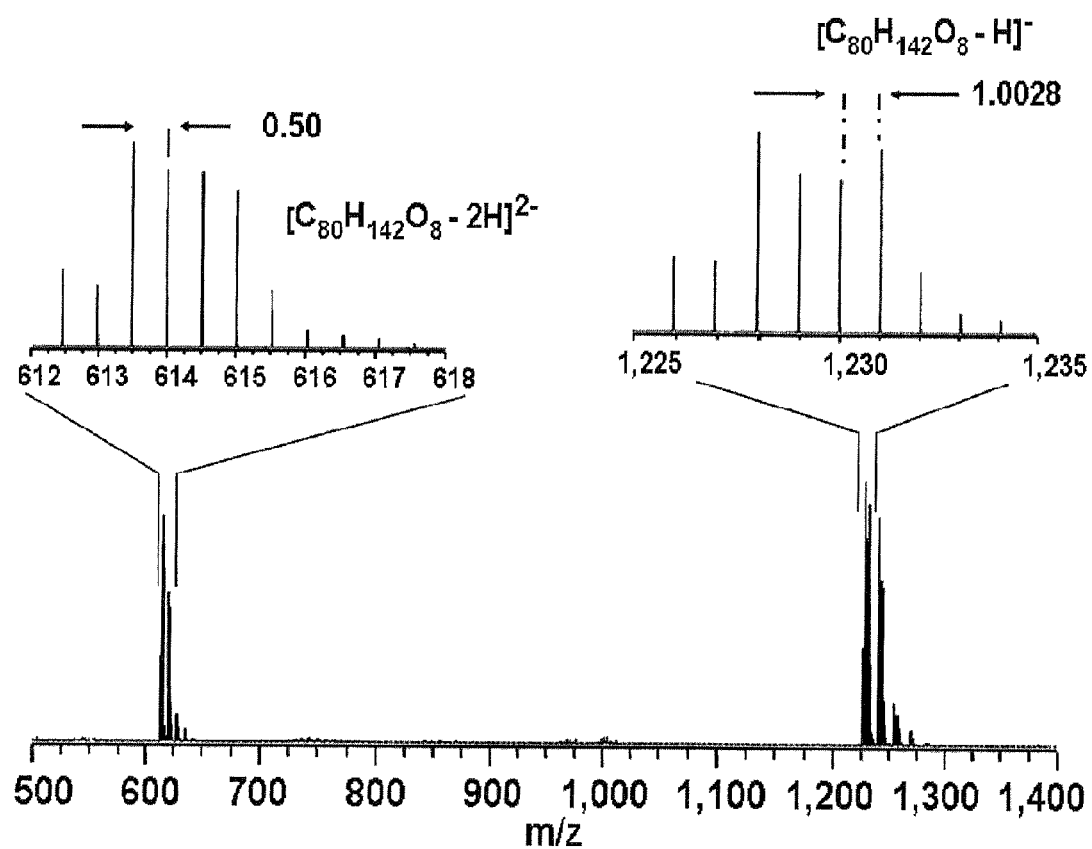

FIGS. 3a and 3b show negative-ion FT-ICR mass spectra of a calcium naphthenate deposit. In FIG. 3a, the zoom mass insets reveal the carbon number range (C78-C84) (middle) and DBE/aromaticity range (DBE 8-12) (top) of the ARN species in the deposit. In FIG. 3b, the spectrum clearly exhibits two distinct peaks from ARN acids with a singly charged cluster at m/z 1225-1270 $[M-H]^-$ and a strong doubly charged cluster at m/z 615-630 $[M-2H]^{2-}$ These clusters are highlighted in the mass scale-expanded segments above each cluster. The general composition for the doubly-charged species is $[C_{80}H_{142}O_8{}^-2H^+]^{2-}$, which corresponds to deprotonation of two of the four carboxylic groups from the parent compound $C_{80}H_{142}O_8$. The base (highest-magnitude) peak in the mass spectrum (singly deprotonated) has a mass to charge (m/z) value of 1230.06293, which is consistent with the molecular formula $[C_{80}H_{141}O_8]-$. The peaks correspond to the general formula $[C_{80}H_{142}O_8—H^+]^-$ from the parent compound $C_{80}H_{142}O_8$. Tetraprotic acids comprise all of the singly charged cluster peaks and indicate that ARN acids are a major component in calcium naphthenate deposits. The range of molecular weights indicates that ARN acids in the calcium naphthenate deposits are not one particular acid, but rather a family of acids with a general formula with varying degrees of unsaturation in the hydrocarbon skeleton.

Broadband negative-ion ESI FT-ICR MS analysis of parent crude oils that produce associated calcium naphthenate deposits identified thousands of acidic species in each crude oil. Comparison of the acidic species in the parent crude to those isolated in their associated deposits revealed that species characteristic of the deposit are at low relative abundance or unobservable in the broadband mass spectrum. Thus, preconcentration of the acidic species in the parent crude is necessary. Conventional ion exchange extraction of acidic species from crude oil is time-consuming and may alter the in situ acid profile of the parent crude through irreversible absorption to the ion exchange resin. Therefore, a modified extraction method was used to isolate acidic species from the parent crude. In order to test the broadband and extraction based detection limits for ARN acids in the parent crudes with associated calcium naphthenate deposits, known amounts of ARN acid were spiked into both the parent crudes and a bitumen sample that does not contain native ARN acids. Based on these experiments, the specific naphthenic acid species present in commercial naphthenic acid deposits were identified.

EXAMPLE 3

Materials and Methods for Evaluation of Naphthenate Deposits

Four calcium naphthenate deposits from different geographical origin were collected from production separators in which naphthenate deposition had been reported. HPLC grade toluene, methanol, methylene chloride, hydrochloric acid (Fisher Scientific), anhydrous magnesium sulfate ($MgSO_4$) and (>99.99% purity) anhydrous ammonia (Sigma-Aldrich) were used as supplied.

Extraction of Naphthenic Acids from Naphthenate Deposits

Calcium naphthenate samples were preweighed (~5-10 g) and washed with toluene to remove entrapped crude oil. The samples were washed interchangeably with toluene and methylene chloride, with the toluene wash being the most applied. The samples were repeatedly washed until the color of the toluene phase was almost clear. To eliminate any trace water problems, petroleum ether may be used as an alternative extraction solvent because water is insoluble in it whereas toluene is soluble in water (0.47 g/L at 20-25°).

After the calcium naphthenate deposits were cleaned, they were digested in aqueous 1 M hydrochloric acid (HCl) followed by toluene extraction. The ratio of the organic phase to aqueous phase was 2:1 by volume. The ARN type naphthenic acids are chemically bound as naphthenate and thus are converted to free acids during the acid digestion. Hence, the free acids are soluble in the organic phase, leaving the counterions (e.g. metal ions) in the aqueous phase. The organic phase was dried in anhydrous magnesium sulfate ($MgSO_4$) to remove any trace water from the aqueous phase. The dry organic phase was then subjected to a reaction with ammonia in custom built deposition reaction cell.

Quantitation

Acid extracts were diluted to 1 mg/mL in standard ESI spray mix for hydrocarbon analysis 50:50 (vol:vol) toluene: methanol for mass spectrometric analysis. A representative aliquot (1 mL) of each sample was spiked with 10 μL of 20% ammonium hydroxide ($NH_4OH$) in methanol to facilitate in the deprotonation of the ARN type naphthenic acids. Each sample was delivered to the mass spectrometer ionization source via a syringe pump at a rate of 400 nL/min through a 50 μm inner diameter fused silica micro ESI needle under typical ESI conditions (needle voltage, 2.0 kV; tube lens, 350 V; and heated capillary current, 4.20 A).

For high resolution analysis, each sample was analyzed with a custom-built 9.4 T 22 cm horizontal room temperature bore diameter (Oxford Corp., Oxford Mead, UK) FT-ICR mass spectrometer. A Modular ICR Data Acquisition system (MIDAS) was used to collect, and process ICR data. Low resolution measurements were performed on an LTQ (ThermoFisher) ion trap.

Results and Discussion

Analysis of the acid extracts from calcium naphthenate deposits universally identifies ARN acids, which are believed to participate in formation of commercial naphthenate deposits. Acidic oxygenated species are the major components in calcium naphthenate deposits and mostly are tetra-carboxylic acids presumed to be ARN acids.

Figure 4A:
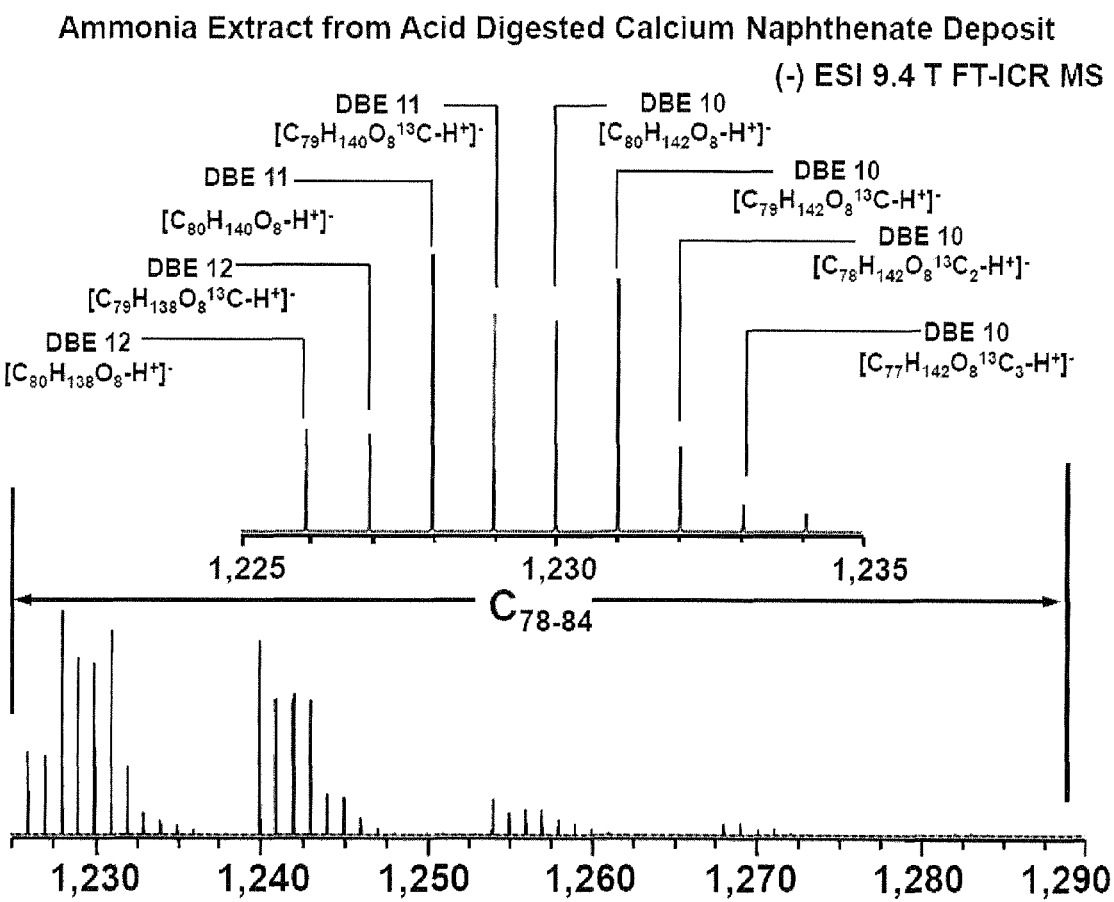
FIGS. 4a and 4b are negative-ion ESI FT-ICR mass spectra of the ammonia extract from an acid digested calcium naphthenate field deposit sample, with FIG. 4a being a zoom mass inset of FIG. 4b.
Figure 4B:
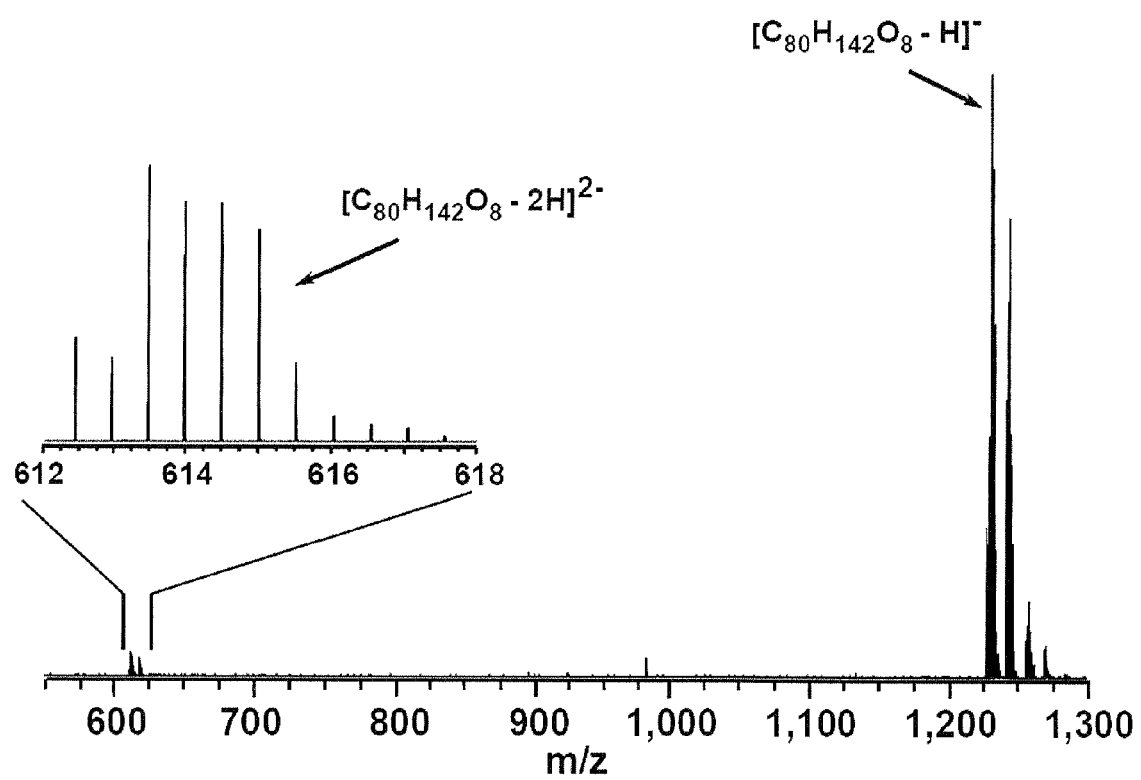

FIGS. 4a and 4b show broadband negative-ion FT-ICR mass spectra of an acid extract from calcium naphthenate sample #1 (CaNaph #1). In FIG. 4b, the spectra clearly exhibit two distinct groups of peaks from ARN acids: a singly charged $[M-H]^-$ family of m/z 1225-1270 and doubly charged $[M-2H]^{2-}$ ions of m/z 615-630. The general composition for the latter species is $[C_{80}H_{142}O_8—2H]^{2-}$, formed by deprotonation of two of the four carboxylic groups in the parent compound $C_{80}H_{142}O_8$. The highest-magnitude peak in the mass spectrum has m/z 1230.06293, consistent with the molecular formula $[C_{80}H_{141}O_8]^-$, i.e., $[C_{80}H_{142}O_8—H]^-$ from deprotonation of the original neutral precursor $C_{80}H_{142}O_8$. Similar to FIGS. 3a and b, the ammonia extracted materials exhibit similar carbon number and aromaticity (DBE) ranges as the species previously identified from the acid digestion of the field deposit. Simply, the ammonia precipitation has no effect (other than significant preconcentration) on the ARN species detected from the deposit.

Figure 5:
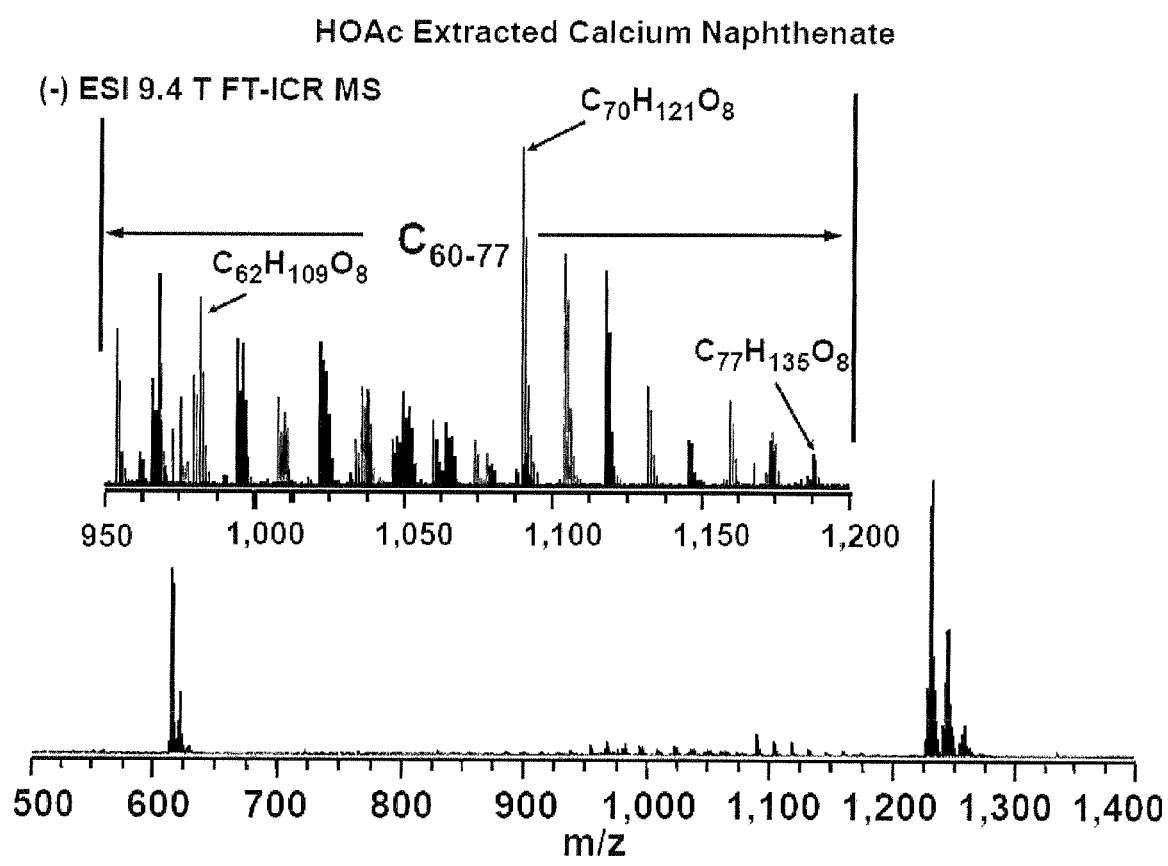
FIG. 5 is a broadband negative-ion ESI 9.4 T FT-ICR mass spectrum of acid extracts from a calcium naphthenate sample below a mass scale-expanded segment, 950-1225 Da, showing some assigned molecular formulas for some low molecular weight ARN acid species.
Figure 6:
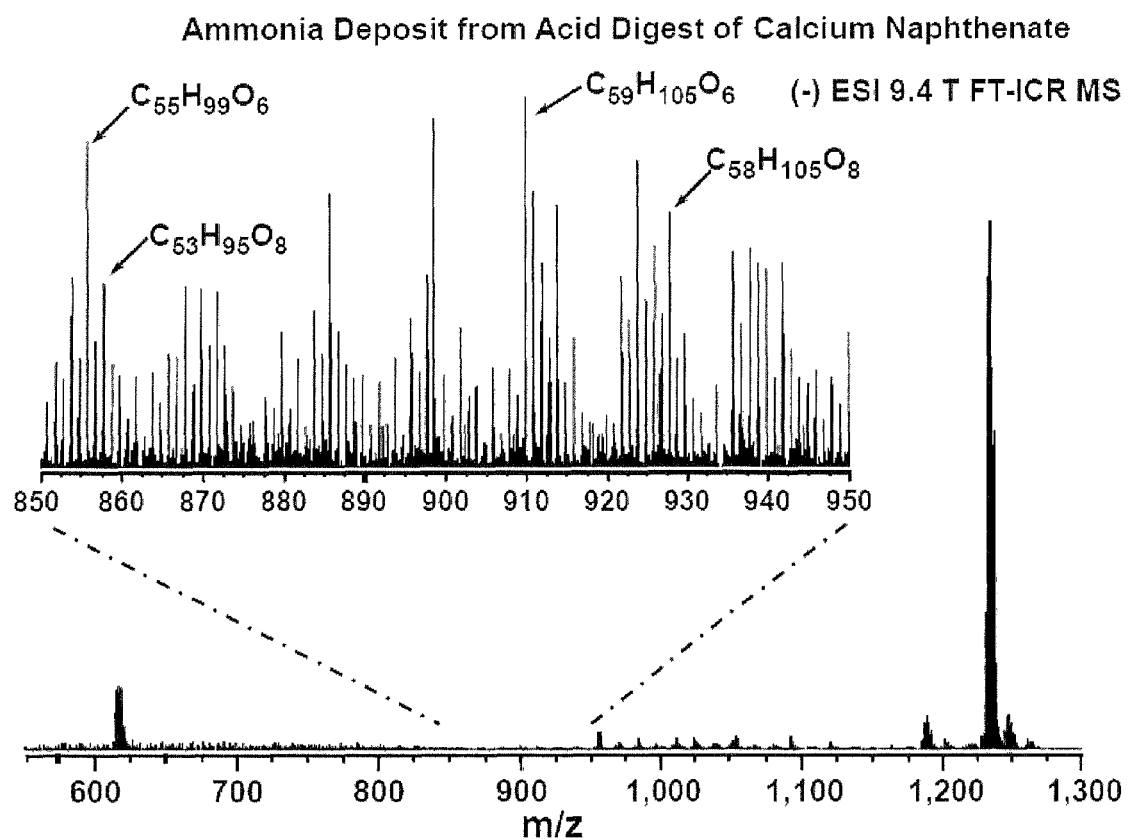
FIG. 6 is a broadband negative-ion ESI 9.4 T FT-ICR mass spectrum of ammonia precipitants isolated from the acid digestion of a calcium naphthenate sample below a mass scale-expanded segment, 850-950 Da, showing some assigned molecular formulas for some low molecular weight ARN acid species and tricarboxylic acid (O6) species.

FIG. 5 shows broadband mass ESI 9.4 Tesla FT-ICR negative-ion mass spectra of an acidic digested calcium naphthenate sample #2 (CaNaph #2) at mass range 500<m/z<1400. The mass scale-expanded segment at mass range 950<m/z<1225 in FIG. 5, top shows low molecular weight ARN acid species tetra-carboxylic acids (i.e. contain 8 oxygen atoms) with a $C_{60-79}$ hydrocarbon skeleton and DBE=8. FIG. 6 shows the broadband mass spectrum obtained from the ammonia extraction of the acid digested calcium naphthenate deposit. The mass scale-expanded segment at mass range 850<m/z<950 FIG. 6 (inset) shows low molecular weight ARN acid species previously not identified, tetra-carboxylic acids (i.e. contain 8 oxygen atoms) with a $C_{53-59}$ hydrocarbon skeleton and with a DBE range of 5-8. These low molecular weight ARN acids were seen only in acid extracts from calcium naphthenate sample #4 (CaNaph #4). The mass scale-expanded segment in FIG. 6 also shows tri-carboxylic acid (i.e. contain 6 oxygen atoms, $O_6$) species which were identified in acid extracts from calcium naphthenate sample #4 (CaNaph #4). The tricarboxylic acid species have a $C_{55-81}$ hydrocarbon skeleton and DBE range of 5-10. Even though all the acid extracts from the calcium naphthenate deposits have tricarboxylic acids, acid extract from calcium naphthenate sample #4 (CaNaph #4) has a higher relative abundance of tricarboxylic acids. Heteroatom class composition analysis confirms that the acid extracts from the calcium naphthenate deposits include ARN acids with a $C_{80}$ hydrocarbon skeleton.

Figure 7A:
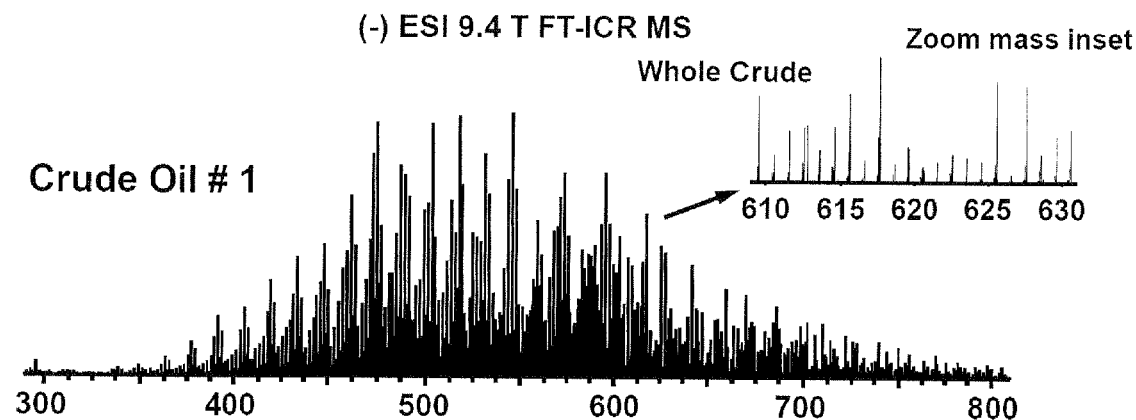
FIG. 7a is a high resolution broadband mass spectrum of a crude oil with known naphthenate deposition problems.
Figure 7B:
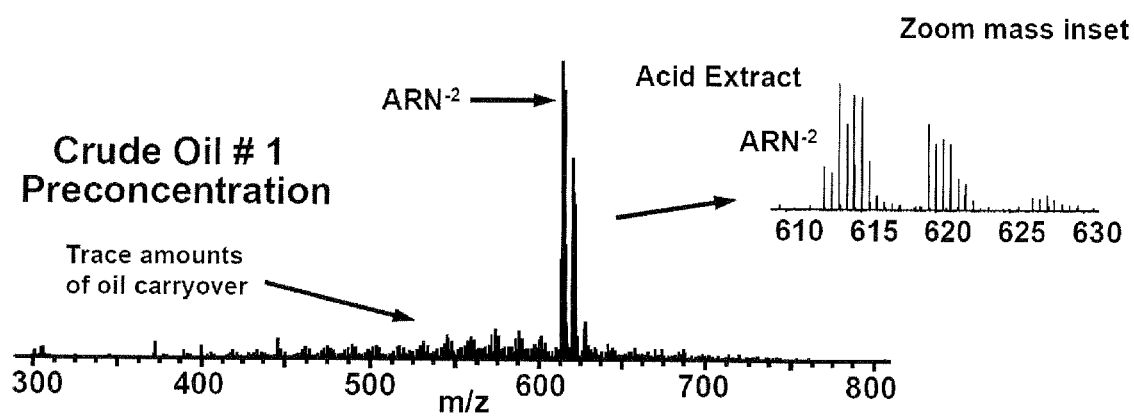
FIG. 7b is a high resolution broadband mass spectrum of the same crude oil subjected to ammonia extraction.
Figure 8A:
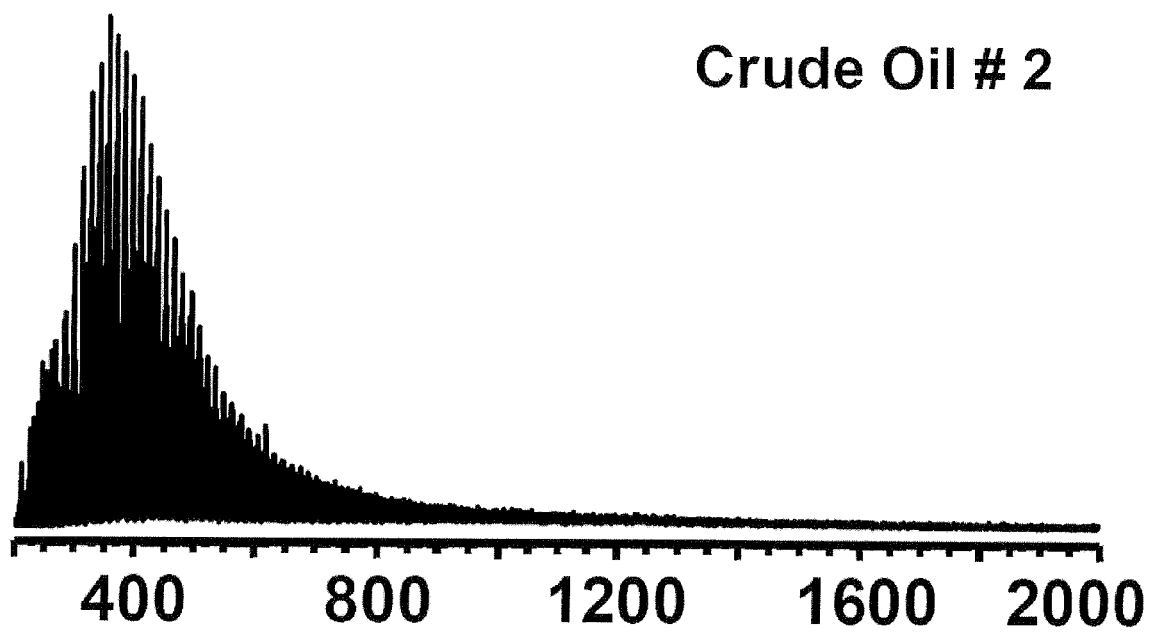
FIGS. 8a and 8c are low resolution mass spectra of two crude oils known to have calcium naphthenate deposition issues.
Figure 8B:
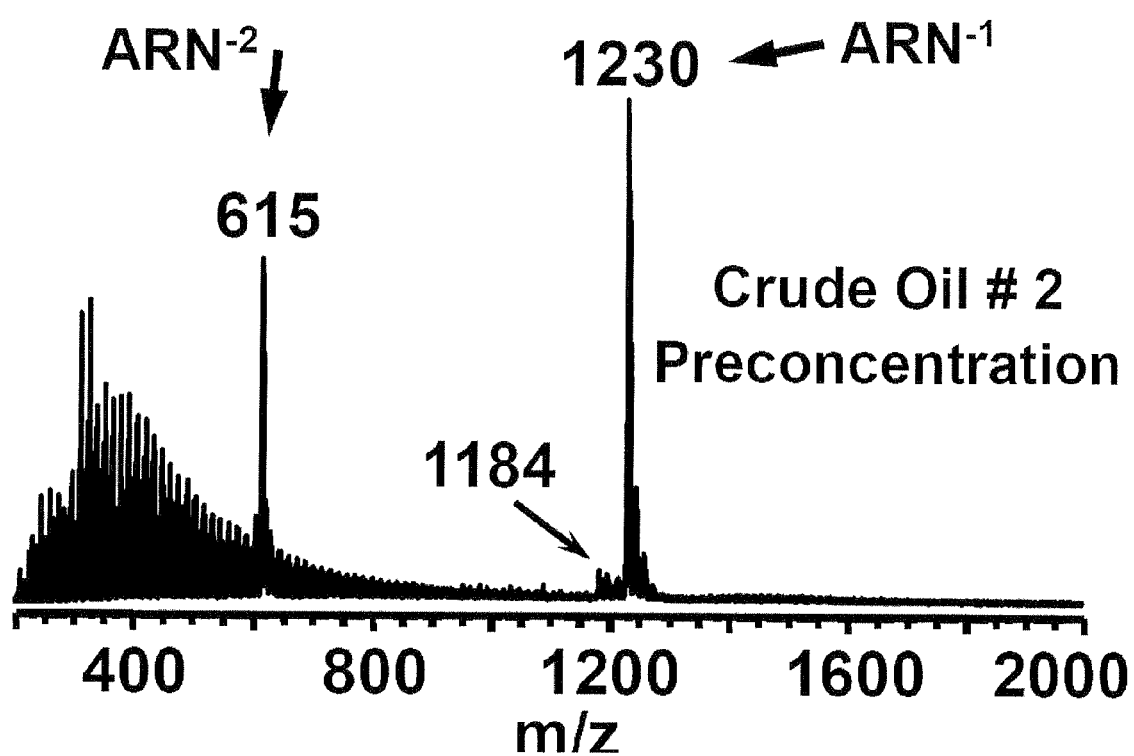
FIGS. 8b and 8d are low resolution mass spectra of the same two crude oils subjected to ammonia extraction.
Figure 8C:
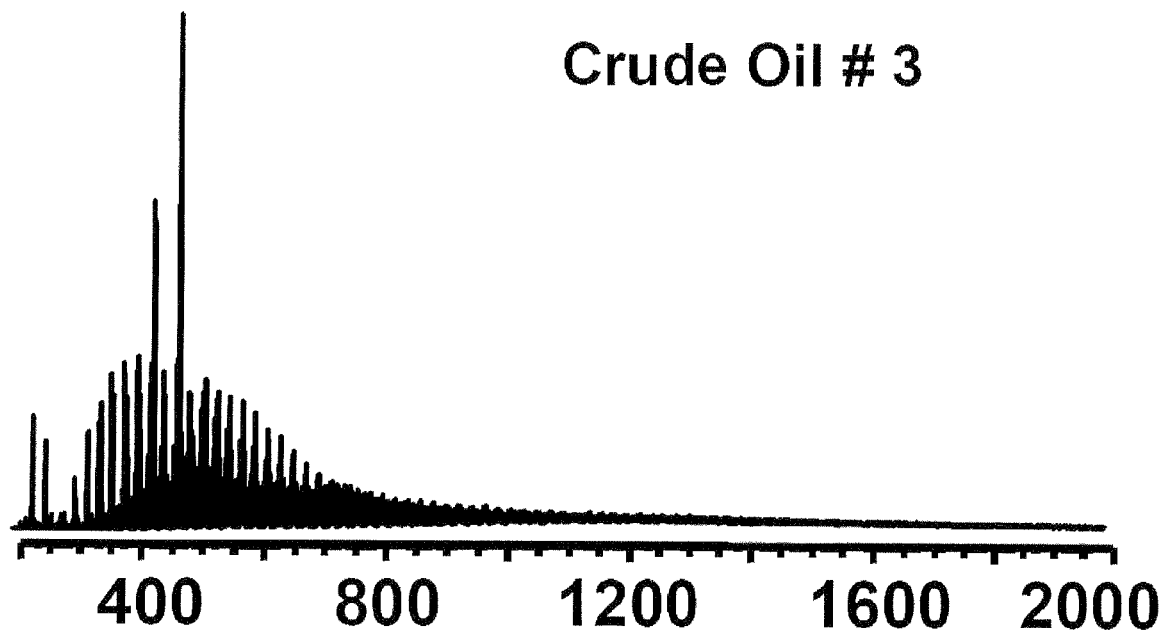
Figure 8D:
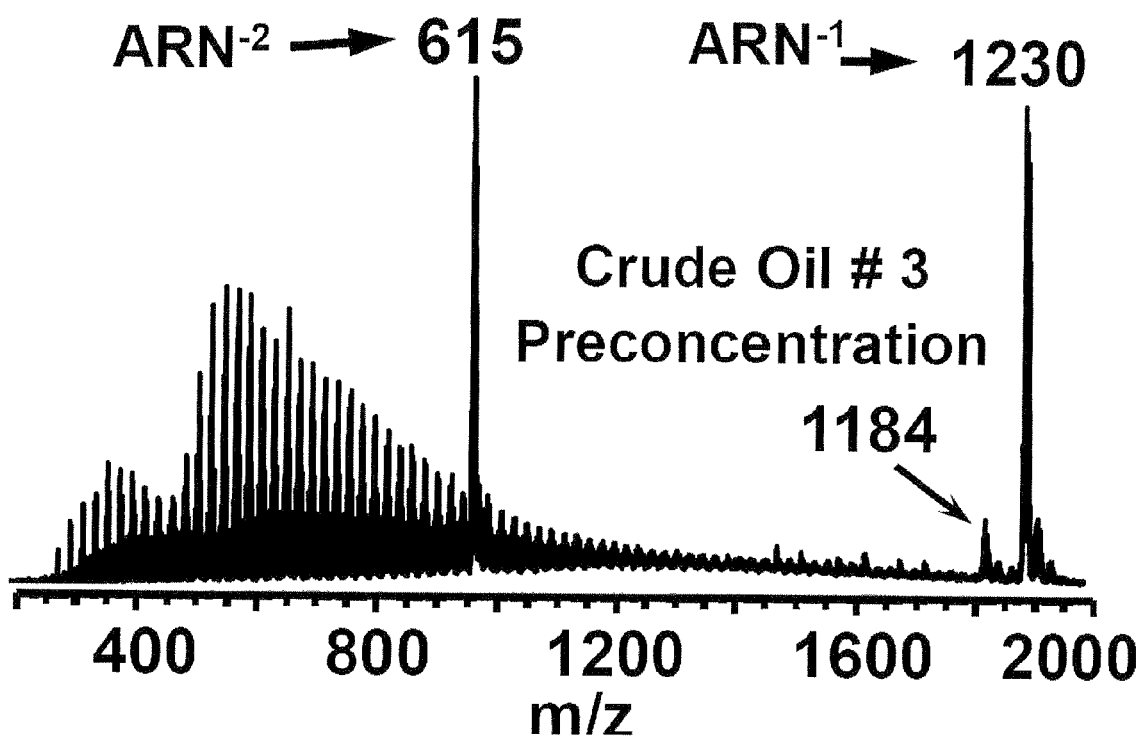

Additional experiments have determined that the mere presence of naphthenic acids known to produce naphthenate deposits in a crude oil composition does not guarantee that the crude oil composition will form commercial naphthenate deposits. However, a survey of 10 crude oils, with 4 exhibiting commercial naphthenate deposits and 6 exhibiting no commercial naphthenate deposits, demonstrated that all of the crude oil compositions exhibiting commercial naphthenate deposits formed naphthenic acids containing deposits when ammonia was bubbled through the crude oil composition. FIGS. 7 and 8 demonstrate the utility of the ammoniated extraction procedure for the evaluation of potential naphthenate deposition from whole crude oils. FIG. 7a shows the broadband (−) ESI FT-ICR mass spectrum of a whole crude oil that has known naphthenate deposit problems. The zoom inset reveals that the characteristic masses associated with the ARN tetraprotic acid species are not detectable in the whole crude. However, after ammonia extraction (FIG. 7b) the doubly deprotonated ARN species is the largest peak in the broadband mass spectrum and is easily identified. Similarly, FIGS. 8a and 8c show the broadband low resolution mass spectra for 2 additional oils known to have naphthenate deposition problems. Neither oil #2 (FIG. 8a) nor oil #3 (FIG. 8c) contain detectable amounts of ARN species. However, after ammonia extraction (FIGS. 8b and 8d), both the singly and doubly deprotonated ARN species are readily identifiable.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method for quantifying the presence of naphthenic acids in a hydrocarbon-comprising liquid, the method comprising:
   contacting a hydrocarbon-comprising liquid with gaseous ammonia to produce a reaction product;
   aging the reaction product of said contacting step by cooling said hydrocarbon-comprising liquid to a temperature of 10° C. or less for a period sufficient to form the reaction product as a precipitate, an emulsion, or both;
   isolating the reaction product produced by said aging step;
   analyzing said reaction product for the presence of naphthenates using a mass spectrometry technique.

2. The method of claim 1, wherein said hydrocarbon-comprising liquid comprises crude oil.

3. The method of claim 1, wherein a duration of said contacting step is sufficient to cause the reaction product to comprise an ammonium naphthenate salt if said hydrocarbon-comprising liquid comprises a naphthenic acid.

4. The method of claim 3, wherein said duration is at least thirty minutes.

5. The method of claim 1, wherein said mass spectrometry technique comprises a Fourier transform ion cyclotron resonance mass spectrometer, an ion trap mass spectrometer, a quadrupole mass spectrometer, an orbitrap mass spectrometer, a time-of-flight mass spectrometer or a magnetic sector mass spectrometer.

6. The method of claim 1, wherein said mass spectroscopy technique comprises an ionization technique selected from the group consisting of electrospray ionization, photoionization, chemical ionization, electron ionization, fast atom bombardment ionization, field ionization, field desorption/ionization, or a combination thereof.

7. The method of claim 1, wherein said analyzing step comprises comparing mass spectrometry results of said reaction product to standards for naphthenic acids known to form commercial naphthenate deposits.

8. The method of claim 7, wherein said naphthenic acids known to form commercial naphthenate deposits comprise (i) ions of tetraprotic carboxylic acids having molecular weights ranging from 1225 to 1270 Daltons, (ii) n-alkyl or branched carboxylic acids having molecular weights ranging from 250 to 650 Daltons, or (iii) both.

9. The method of claim 7, wherein said naphthenic acids known to form commercial naphthenate deposits comprise tetraprotic carboxylic acids of Formula I:

$$C_nH_{2(n+1-DBE)}O_8$$

wherein: n=77-85, and DBE (double bond equivalent)=8-12.

10. The method of claim 1, wherein said reaction product is a precipitate, an emulsion, or both.

11. A method for determining whether a crude oil composition will produce commercial naphthenate deposits during crude oil processing, comprising:
  contacting a crude oil composition with gaseous ammonia to produce a reaction product;
  aging the reaction product of said contacting step by cooling the crude oil composition to a temperature of 10° C. or less for a period sufficient to form the reaction product as a precipitate, an emulsion, or both;
  isolating the reaction product produced by said aging step;
  analyzing said reaction product for the presence of naphthenic acid salts with a mass spectrometry technique, said analyzing step comprising:
    comparing mass spectrometry results of said reaction product to standards for naphthenic acids known to form commercial naphthenate deposits.

12. The method of claim 11, wherein said naphthenic acids known to form commercial naphthenate deposits comprise (i) ions of tetraprotic carboxylic acids having a molecular weight ranging from 1225 to 1270 Daltons, (ii) n-alkyl or branched carboxylic acids having molecular weights ranging from 250 to 650 Daltons, or (iii) both.

13. The method of claim 11, wherein a duration of said contacting step is sufficient to produce a reaction product comprising an ammonium naphthenate salt in said hydrocarbon-comprising liquid comprises a naphthenic acid.

14. The method of claim 11, wherein said mass spectrometry technique comprises a Fourier transform ion cyclotron resonance mass spectrometer, an ion trap mass spectrometer, a quadrupole mass spectrometer, an orbitrap mass spectrometer, a time-of-flight mass spectrometer or a magnetic sector mass spectrometer.

15. The method of claim 11, wherein said mass spectroscopy technique comprises an ionization technique selected from the group consisting of electrospray ionization, photoionization, chemical ionization, electron ionization, fast atom bombardment ionization, field ionization, field desorption/ionization, or a combination thereof.

16. A method of operating a crude oil operation to avoid the formation of naphthenate deposits, comprising:
  contacting a crude oil mixture used in a crude oil operation with gaseous ammonia to produce a reaction product;
  aging the reaction product of said contacting step by cooling the crude oil mixture to a temperature of 10° C. or less for a period sufficient to form the reaction product as a precipitate, an emulsion, or both;
  isolating the reaction product produced by said aging step;
  analyzing said reaction product for the presence of naphthenic acid ions present in commercial naphthenate deposits with a mass spectrometry technique;
  comparing mass spectrometry results from said analyzing step to mass spectrometry standards for naphthenic acid ions present in commercial naphthenate deposits; and
  adjusting the composition of the crude oil mixture to reduce the formation of commercial naphthenate deposits if said comparing step indicates said reaction product comprises a naphthenic acid ion present in commercial naphthenate deposits.

17. The method of claim 16, wherein said crude oil mixture comprises production water and said treating step comprises, (i) modifying a pH of said production water, (ii) reducing in said production water a concentration of one or more ions selected from the group consisting of $HCO^{3-}$, $Ca^{2+}$, $Fe^{2+}$, $Mg^{2+}$, $Na^+$ and $K^+$, or (iii) both.

18. The method of claim 16, wherein said naphthenic acid ions present in commercial naphthenate deposits comprise (i) ions of tetraprotic carboxylic acids having molecular weights ranging from 1225 to 1270 Daltons, (ii) n-alkyl or branched carboxylic acids having molecular weights ranging from 250 to 650 Daltons, or (iii) both.

* * * * *